United States Patent
Chang

(10) Patent No.: US 8,538,723 B2
(45) Date of Patent: Sep. 17, 2013

(54) EXERCISE MODE AUTOMATIC IDENTIFICATION METHOD

(75) Inventor: Cheng-Lii Chang, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 358 days.

(21) Appl. No.: 12/957,773

(22) Filed: Dec. 1, 2010

(65) Prior Publication Data

US 2012/0072164 A1 Mar. 22, 2012

(30) Foreign Application Priority Data

Sep. 20, 2010 (TW) .............................. 99131882 A

(51) Int. Cl.
*G01P 15/00* (2006.01)
*A63B 71/00* (2006.01)

(52) U.S. Cl.
USPC .................................. 702/141; 482/8; 73/488

(58) Field of Classification Search
USPC .............. 702/141, 33, 66–68, 70–71, 81, 84, 702/127, 149–153, 160, 179, 182–183, 188–189; 482/7–9, 52, 54, 57, 74; 73/1.37, 488, 492
See application file for complete search history.

(56) References Cited

U.S. PATENT DOCUMENTS

| 5,899,963 | A | 5/1999 | Hutchings |
| 6,145,389 | A | 11/2000 | Ebeling et al. |
| 7,162,392 | B2 | 1/2007 | Vock et al. |
| 7,713,173 | B2 | 5/2010 | Shin et al. |
| 7,715,982 | B2 | 5/2010 | Grenfell et al. |
| 2002/0022551 | A1 | 2/2002 | Watterson et al. |
| 2010/0120584 | A1* | 5/2010 | Oshima et al. ................. 482/8 |

FOREIGN PATENT DOCUMENTS

| TW | 516949 | 1/2003 |
| TW | 200628194 | 8/2006 |
| TW | 200630587 | 9/2006 |
| TW | 200729051 | 8/2007 |
| TW | M332833 | 5/2008 |
| TW | M344892 | 11/2008 |
| TW | M362402 | 8/2009 |
| TW | 200951868 | 12/2009 |
| TW | M370138 | 12/2009 |
| TW | I321057 | 3/2010 |
| TW | 201017134 | 5/2010 |
| TW | M379552 | 5/2010 |
| TW | 201020516 | 6/2010 |
| TW | I325491 | 6/2010 |

OTHER PUBLICATIONS

Chung-Fu Kao, "Orientation Estimation Using Coplanar Accelerometers and Magnetic Sensors", A Thesis, National Chiao Tung University, Jul. 2006, pp. 1-84.

(Continued)

*Primary Examiner* — Toan Le
(74) *Attorney, Agent, or Firm* — Muncy, Geissler, Olds & Lowe, PLLC

(57) ABSTRACT

An exercise mode automatic identification method is provided. The automatic identification method includes the following steps. A step count taken by a user is obtained. A horizontal transient speed at which the user moves at the end of a predetermined period is obtained. The user's exercise mode is defined by a microprocessor according to the step count and the horizontal transient speed.

10 Claims, 4 Drawing Sheets

(56) References Cited

OTHER PUBLICATIONS

Po-Min Shi, "SONFIN for Physical Activities Classification with Accelerometer", Jan. 2009, pp. 1-65.

Zhe-Min Zhong, "Accelerometer Based Gesture Recognitiion System and Its Applications", Jul. 2008, pp. 1-68.

Jian-Chong Shi, "The Implemenation of a G-Sensor-based Pedometer", Jan. 2010, pp. 1-61.

* cited by examiner

EXERCISE MODE AUTOMATIC IDENTIFICATION METHOD

This application claims the benefit of Taiwan application Serial No. 99131882, filed Sep. 20, 2010, the subject matter of which is incorporated herein by reference.

BACKGROUND

1. Technical Field

The disclosure relates in general to an automatic identification method, and more particularly to an exercise mode automatic identification method.

2. Description of the Related Art

As health awareness arises universally, exercise culture is now popular everywhere. Examples of popular exercise include walking, jogging, running on the treadmill, cycling, and swimming.

The current aids for exercise management can gather statistics with respect to one single exercise mode. Let the pedometer be taken for example. The pedometer can only calculate the step count, but cannot determine the exercise mode or record and analyze the user's various exercise modes. Thus, the user stand still cannot effectively perform exercise management with these aids.

SUMMARY

The disclosure is directed to an exercise mode automatic identification method. The user's exercise mode is defined according to the step count and the horizontal transient speed, so that the user's various exercise modes can be recorded and analyzed.

According to a first aspect of the present disclosure, an exercise mode automatic identification method is provided. The automatic identification method includes the following steps. A step count taken by a user is obtained. A horizontal transient speed at which the user moves at the end of a predetermined period is obtained. The user's exercise mode is defined by a microprocessor according to the step count and the horizontal transient speed.

The above and other aspects of the disclosure will become better understood with regard to the following detailed description of the non-limiting embodiment(s). The following description is made with reference to the accompanying drawings.

DETAILED DESCRIPTION

Figure 1:
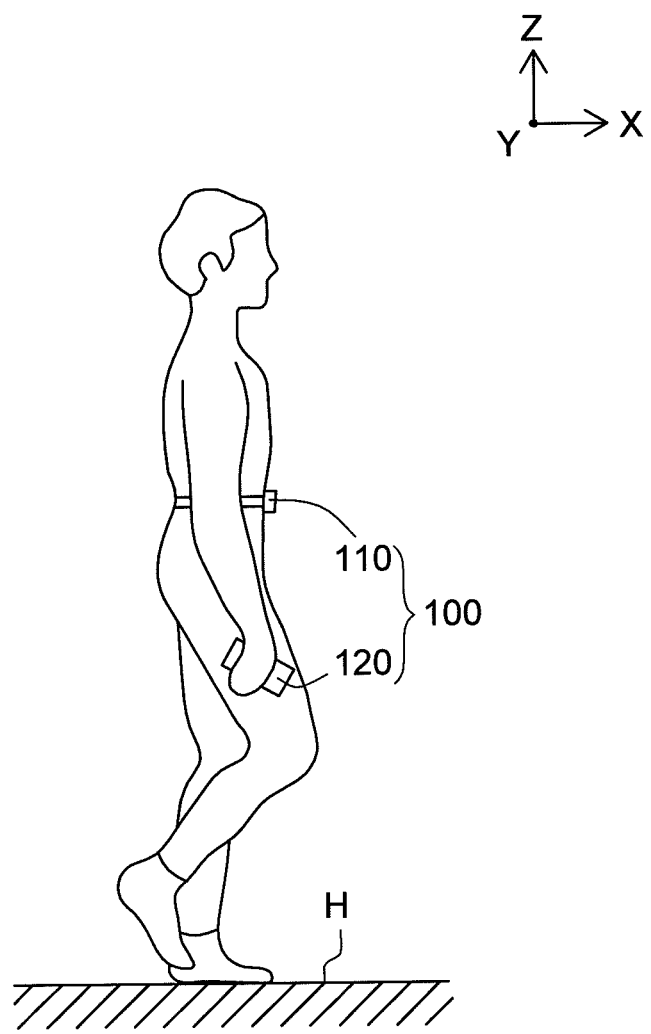
FIG. 1 shows an exercise mode automatic identification system according to an embodiment of the disclosure.

Referring to FIG. 1, an exercise mode automatic identification system 100 according to an embodiment of the disclosure is shown. The automatic identification system 100 includes a measurement device 110 and a microprocessor 120. The measurement device 110, used for measuring the user's exercise information, can be appended to the part of the torso which is not affected by the movement of the limbs such as the waist or the chest. The microprocessor 120 analyzes exercise information to identify the user's exercise mode. In an embodiment, the microprocessor 120 can be integrated in a mobile phone or a notebook computer. The exercise information can be transmitted between the measurement device 110 and the microprocessor 120 wirelessly or via the cable. When the measurement device 110 and the microprocessor 120 are separated, the measurement device 110 can be easily disposed at a suitable position, and the microprocessor 120 being held at hand can display the analysis result. In another embodiment, the measurement device 110 and the microprocessor 120 can be integrated in the same electronic device. When the measurement device 110 and the microprocessor 120 are integrated, the cost and volume of automatic identification system 100 can be further reduced. Whether the automatic identification system 100 should adopt separation design or integration design and what device should the automatic identification system 100 be integrated with are determined according to the needs of the products.

Figure 2A:
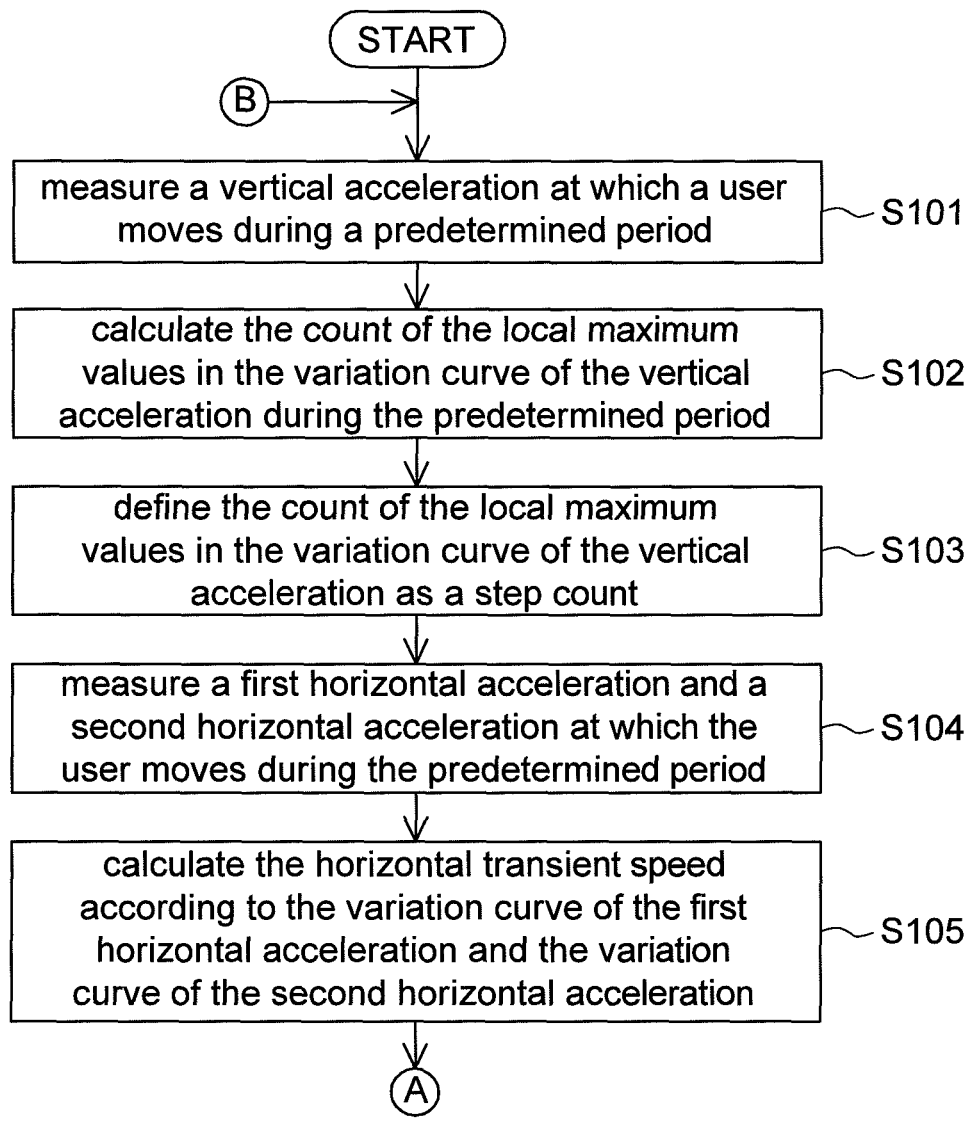
FIGS. 2A-2B show a flowchart of an exercise mode automatic identification method according to an embodiment of the disclosure.
Figure 2B:
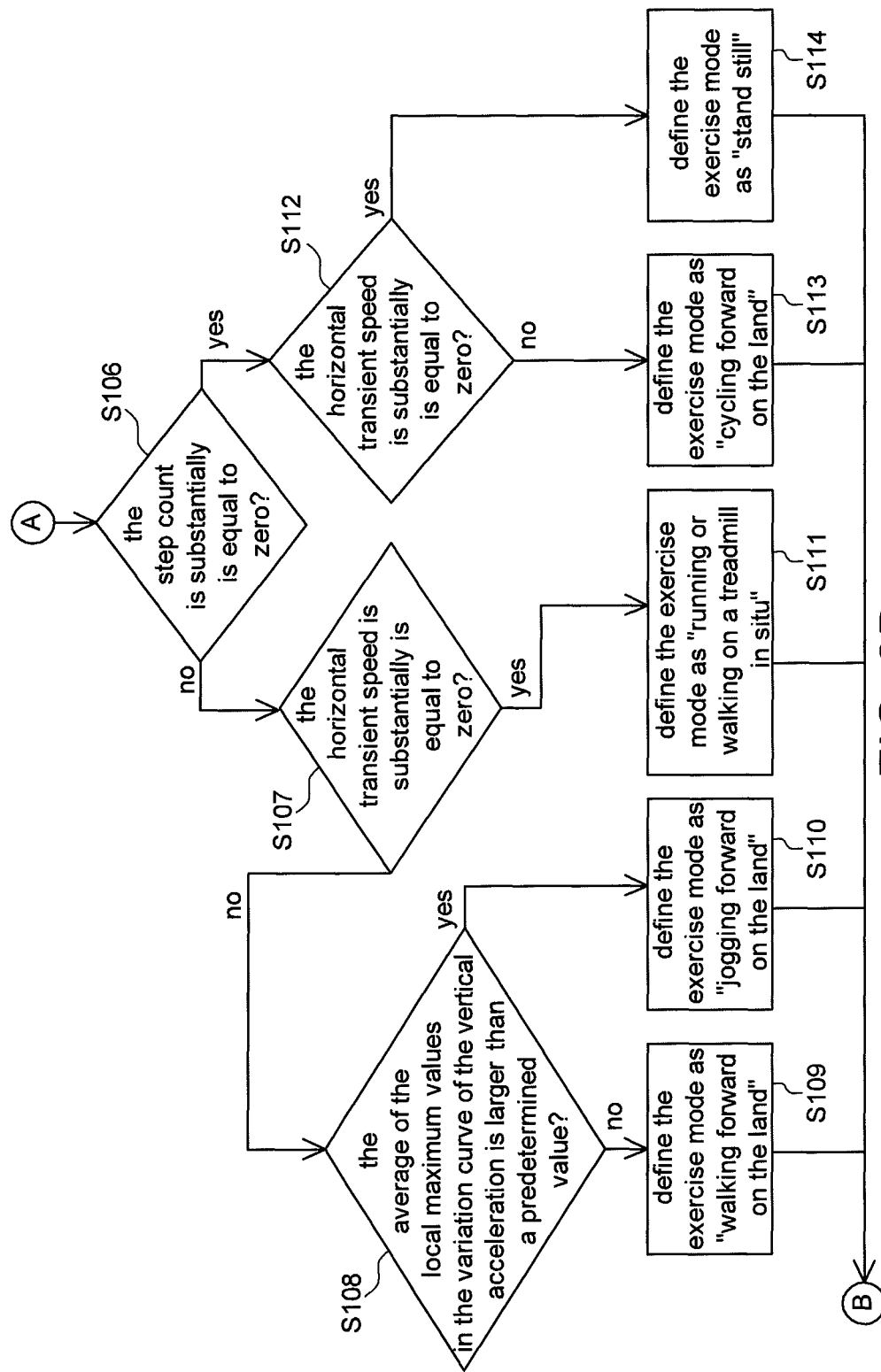

Referring to FIGS. 2A-2B, a flowchart of an exercise mode automatic identification method according to an embodiment of the disclosure is shown. The automatic identification method of the present embodiment of the disclosure is exemplified below with the automatic identification system 100 of FIG. 1. However, anyone who is skilled in the disclosure will understand that the automatic identification method of the embodiment of the disclosure is not limited to the automatic identification system 100 of FIG. 1.

Firstly, in steps S101-S103, a step count taken by a user during a predetermined period is measured by a measurement device 110, wherein the predetermined period is such as 10 seconds. In steps S101-S103, the measurement device 110 can obtain the step count via a mechanic pedometer or a tri-axial accelerometer. In the present embodiment of the disclosure, steps S101-S103 are exemplified by a tri-axial accelerometer.

Figure 3:
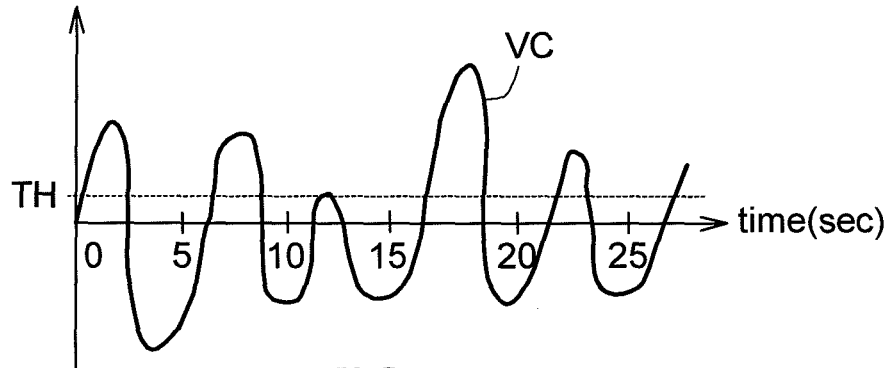
FIG. 3 shows a variation curve of a vertical acceleration which varies with the time according to an embodiment of the disclosure.

In step S101, the vertical acceleration at which the user moves during the predetermined period is measured by the measurement device 110 (such as a tri-axial accelerometer). The vertical acceleration is substantially perpendicular to a horizontal surface (such as the Z-axis forward direction or the Z-axis backward direction of FIG. 1). In the present step, one axis of the tri-axial accelerometer is directed to the ground or the sky, and the vertical acceleration is continuously sensed during the predetermined period. The vertical acceleration obtained by the measurement device 110 is further transmitted to the microprocessor 120. The vertical acceleration varying with the time is illustrated by the variation curve VC of FIG. 3.

In step S102, the count of the local maximum values in the variation curve VC of the vertical acceleration during the predetermined period is calculated by the microprocessor 120. Let FIG. 3 be taken for example. Between the $10^{th}$-$20^{th}$ second, the count of the local maximum values in the variation curve VC of the vertical acceleration is 2.

Next, in step S103, the count of the local maximum values in the variation curve VC of the vertical acceleration is defined as the step count by the microprocessor 120. For example, in steps S102-S103, the step count taken by the user between the $10^{th}$-$20^{th}$ second is determined as 2, which is the count of the local maximum values in the variation curve VC of the vertical acceleration.

In steps S104-S105, a horizontal transient speed at which the user moves at the end of the predetermined period is measured by the measurement device 110. In the present embodiment of the disclosure, steps S104-S105 are exemplified by a tri-axial accelerometer or a bi-axial accelerometer.

Figure 4A:
FIG. 4A shows a variation curve of the first horizontal acceleration which varies with the time according to an embodiment of the disclosure.
Figure 4B:
FIG. 4B shows a variation curve of the second horizontal acceleration which varies with the time according to an embodiment of the disclosure.

In step S104, a first horizontal acceleration and a second horizontal acceleration at which the user moves during the predetermined period are measured by the measurement device 110 (such as a tri-axial accelerometer or a bi-axial accelerometer). In the present step, the first horizontal acceleration and the second horizontal acceleration are substantially perpendicular to each other, and are all substantially parallel to a horizontal surface H (illustrated in FIG. 1). The direction of the first horizontal acceleration is such as the X-axis forward direction of FIG. 1, and the direction of the second horizontal acceleration is such as the Y-axis forward direction of FIG. 1. The first horizontal acceleration and the second horizontal acceleration that are obtained by the measurement device 110 are further transmitted to the microprocessor 120. The first horizontal acceleration varying with the time is illustrated in the variation curve LC1 of FIG. 4A. The second horizontal acceleration varying with the time is illustrated in the variation curve LC2 of FIG. 4B.

In step S105, the horizontal transient speed is calculated by the microprocessor 120 according to the variation curve LC1 of the first horizontal acceleration and the variation curve LC2 of the second horizontal acceleration. The microprocessor 120 can integrate the variation curve LC1 of the first horizontal acceleration and the variation curve LC2 of the second horizontal acceleration first, and then calculate the horizontal transient speed at which the user moves at the end of the predetermined period through vector sum.

In step S106-S114, the user's exercise mode is defined by the microprocessor 120 according to the step count and the horizontal transient speed. Through the automatic identification method of the present embodiment of the disclosure, various exercise modes such as "walking forward on the land", "jogging forward on the land", "running or walking on a treadmill in situ", "cycling forward on the land" and "stand still" can be defined.

In step S106, whether the step count is substantially equal to zero is determined by the microprocessor 120. If the step count is not equal to zero, then the method proceeds to step S107. If the step count is substantially equal to zero, then the method proceeds to step S112.

In step S107, whether the horizontal transient speed is substantially equal to zero is determined by the microprocessor 120. If the horizontal transient speed is not equal to zero, then the method proceeds to step S108. If the horizontal transient speed is substantially equal to zero, then the method proceeds to step S111.

In step S108, whether the average of the local maximum values in the variation curve VC of the vertical acceleration is larger than a predetermined value TH (marked in FIG. 3) is determined by the microprocessor 120. If the average of the local maximum values in the variation curve VC of the vertical acceleration is not larger than the predetermined value TH, then the method proceeds to step S109. If the average of the local maximum values in the variation curve VC of the vertical acceleration is larger than the predetermined value TH, then the method proceeds to step S110.

In step S109, the exercise mode is defined as "walking forward on the land" by the microprocessor 120. In other words, if the step count is not equal to zero, the horizontal transient speed is not equal to zero and the average of the local maximum values in the variation curve VC of the vertical acceleration is not larger than the predetermined value TH, it can be determined that the user takes steps and moves but the change in steps is not violent. Thus, the user's exercise mode is defined as "walking forward on the land".

In step S110, the exercise mode is defined as "jogging forward on the land" by the microprocessor 120. In other words, if the step count is not equal to zero, the horizontal transient speed is not equal to zero and the average of the local maximum values in the variation curve VC of the vertical acceleration is larger than the predetermined value TH, it can be determined that the user takes steps and moves and the change in steps is violent. Thus, the user's exercise mode is defined as "jogging forward on the land".

In step S111, the exercise mode is defined as "running or walking on a treadmill in situ" by the microprocessor 120. In other words, if the step count is not equal to zero but the horizontal transient speed is substantially equal to zero, it can be determined that the user takes steps but does not move. Thus, the user's exercise mode is defined as "running or walking on a treadmill in situ".

In step S112, whether the horizontal transient speed is substantially equal to zero is determined by the microprocessor 120. If the horizontal transient speed is not equal to zero, then the method proceeds to step S113. If the horizontal transient speed is substantially equal to zero, then the method proceeds to step S114.

In step S113, the exercise mode is defined as "cycling forward on the land" by the microprocessor 120. In other words, if the horizontal transient speed is not equal to zero but the step count is substantially equal to zero, it can be determined that the user moves but does not takes steps. Thus, the user's exercise mode is defined as "cycling forward on the land".

In step S114, the exercise mode is defined as "stand still" by the microprocessor 120. In other words, if the step count is substantially equal to zero, and the horizontal transient speed is also substantially equal to zero, it can be determined that the user neither takes steps nor moves. Thus, the user's exercise mode is defined as "stand still".

When the predetermined period finishes and steps S101-S114 are performed already, the method returns to step S101, the steps S101-S103 of measuring the step count, the steps S104-S105 of measuring the horizontal transient speed and the steps S106-S114 of defining the exercise mode are repeated.

The relationships between the determination terms and the exercise modes are summarized in Table 1 and Table 2 below.

TABLE 1

| | Is the step count substantially equal to zero? | Is the horizontal transient speed substantially equal to zero? |
|---|---|---|
| "walking forward on the land" or "Jogging forward on the land" | No | No |
| "running or walking on a treadmill in situ" | No | Yes |
| "cycling forward on the land" | Yes | No |
| "stand still" | Yes | Yes |

TABLE 2

| | Is the average of the local maximum values in the variation curve VC of the vertical acceleration is larger than a predetermined value TH given that the step count is not equal to zero and the horizontal transient speed is not equal to zero? |
|---|---|
| "walking forward on the land" | No |
| "jogging forward on the land" | Yes |

In the present embodiment of the disclosure, whether the step count is substantially equal to zero is determined before whether the horizontal transient speed is substantially equal to zero is determined. However, in other embodiments, whether the horizontal transient speed is substantially equal to zero can be determined before whether the horizontal transient speed is substantially equal to zero is determined.

After the user has finished series of exercise, the exercise mode in the course of exercise can be immediately recorded for subsequent analysis, and the calorie consumption in each exercise mode can be accurately calculated to improve the accuracy in analysis. For example, the user may walk to a car park, cycle to the office form the car park, park his/her bicycle near the office, and then jogs to the office. The above exercises can be identified and recorded by the automatic identification system and method of the present embodiment of the disclosure. Thus, the user can effectively manage the health information such as calorie consumption.

While the disclosure has been described by way of example and in terms of the exemplary embodiment(s), it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. An exercise mode automatic identification method used for identifying an exercise mode of a user, the automatic identification method comprising:
   obtaining a step count taken by a user;
   obtaining a horizontal transient speed at which the user moves at the end of a predetermined period; and
   defining the user's exercise mode as walking forward on the land, jogging forward on the land, running or walking on a treadmill in situ, or cycling forward on the land by a microprocessor according to the step count and the horizontal transient speed.

2. The exercise mode automatic identification method according to claim 1, wherein the step of obtaining the step count comprises:
   measuring a vertical acceleration at which the user moves during the predetermined period by an accelerometer, wherein the vertical acceleration is substantially perpendicular to a horizontal surface; and
   calculating the step count according to the variation curve of the vertical acceleration.

3. The exercise mode automatic identification method according to claim 2, wherein the accelerometer is a tri-axial accelerometer.

4. The exercise mode automatic identification method according to claim 2, wherein the step of calculating the step count according to the variation curve of the vertical acceleration comprises:
   calculating the count of the local maximum values in the variation curve of the vertical acceleration during the predetermined period; and
   defining the count of the local maximum values in the variation curve of the vertical acceleration as the step count.

5. The exercise mode automatic identification method according to claim 1, wherein the step of obtaining the step count is measured via a mechanic pedometer.

6. The exercise mode automatic identification method according to claim 1, wherein the step of obtaining the horizontal transient speed comprises:
   measuring a first horizontal acceleration and a second horizontal acceleration at which the user moves during the predetermined period by an accelerometer, wherein the first horizontal acceleration and the second horizontal acceleration are substantially parallel to a horizontal surface and perpendicular to each other; and
   calculating the horizontal transient speed according to the variation curve of the first horizontal acceleration and the variation curve of the second horizontal acceleration.

7. The exercise mode automatic identification method according to claim 6, wherein the accelerometer is a tri-axial accelerometer.

8. The exercise mode automatic identification method according to claim 1, wherein the step of automatically defining the exercise mode comprises:
   defining the exercise mode as "jogging forward on the land" or "walking forward on the land" if the step count is not equal to zero and the horizontal transient speed is not equal to zero either;
   defining the exercise mode as "running or walking on a treadmill in situ" if the step count is not equal to zero but the horizontal transient speed is substantially equal to zero; and
   defining the exercise mode as "cycling forward on the land" if the step count is substantially equal to zero but the horizontal transient speed is not equal to zero.

9. The exercise mode automatic identification method according to claim 1, wherein the step of obtaining the step count comprises:
   obtaining a vertical acceleration at which the user moves during the predetermined period by an accelerometer, wherein the vertical acceleration is substantially perpendicular to a horizontal surface;
   calculating the count of the local maximum values in the variation curve of the vertical acceleration during the predetermined period; and
   defining the count of the local maximum values in the variation curve of the vertical acceleration as the step count;
   the step of automatically defining the exercise mode comprises:
   defining the exercise mode as "jogging forward on the land" if the step count is not equal to zero, the horizontal transient speed is not equal to zero and the average of the local maximum values in the variation curve of the vertical acceleration is larger than a predetermined value; and
   defining the exercise mode as "walking forward on the land" if the step count is not equal to zero, the horizontal transient speed is not equal to zero and the average of the local maximum values in the variation curve of the vertical acceleration is not larger than the predetermined value.

10. The exercise mode automatic identification method according to claim 1, wherein the step of obtaining the step count, the step of obtaining the horizontal transient speed and the step of automatically defining the exercise mode are performed repeatedly.

\* \* \* \* \*